(12) United States Patent
Tsengas (10) Patent No.: US 9,220,238 B2
(45) Date of Patent: *Dec. 29, 2015

(54) MOLDED OR EXTRUDED CORK COMPOSITE AND METHOD OF MANUFACTURING COMPRESSED CORK PET PRODUCTS AND PET TOYS MADE FROM THE SAME

(71) Applicant: OurPet's Company, Fairport Harbor, OH (US)

(72) Inventor: Steven Tsengas, Fairport Harbor, OH (US)

(73) Assignee: OURPET'S COMPANY, Fairport Harbor, OH (US)

( * ) Notice: Subject to any disclaimer, the term of this patent is extended or adjusted under 35 U.S.C. 154(b) by 15 days.

This patent is subject to a terminal disclaimer.

(21) Appl. No.: 13/929,855

(22) Filed: Jun. 28, 2013

(65) Prior Publication Data

US 2015/0017118 A1 Jan. 15, 2015

Related U.S. Application Data

(60) Provisional application No. 61/806,417, filed on Mar. 29, 2013.

(51) Int. Cl.

| A01N 25/00 | (2006.01) |
| A01K 29/00 | (2006.01) |
| A01K 15/02 | (2006.01) |
| A01N 65/22 | (2009.01) |
| A01N 43/12 | (2006.01) |

(52) U.S. Cl.
CPC ............. *A01K 15/025* (2013.01); *A01K 15/024* (2013.01); *A01K 29/00* (2013.01); *A01N 25/00* (2013.01); *A01N 43/12* (2013.01); *A01N 65/22* (2013.01)

(58) Field of Classification Search
None
See application file for complete search history.

(56) References Cited

U.S. PATENT DOCUMENTS

| 1,022,113 | A | * | 4/1912 | Smith | ........................ 119/711 |
| 5,797,353 | A | | 8/1998 | Leopold | |
| 7,150,245 | B2 | | 12/2006 | Lamstein | |
| 8,631,768 | B1 | | 1/2014 | Sumitsuji | |
| 2011/0206798 | A1 | | 8/2011 | Loew | |

FOREIGN PATENT DOCUMENTS

| EP | 0 552 897 A1 * | 1/1993 | ............... A23K 1/18 |
| JP | 09-019232 | 1/1997 | |
| JP | 11-155409 | 6/1999 | |
| JP | 2000-069876 | 3/2000 | |
| JP | 2005-279227 | 10/2005 | |

* cited by examiner

*Primary Examiner* — Jeffrey P Palenik
(74) *Attorney, Agent, or Firm* — John D Gugliotta (57) ABSTRACT

A cork-catnip composite material is provided that is capable of being molded, compressed, extruded or similarly processed into small or large bodies or sheets and allow for the economic manufacture of a variety of products for domestic pets, especially felines. Dried and granulated catnip (or similar olfactory attractant) is blended with a fill material such as powdered or granulated agglomerate cork material are then mixed with a bonding agent. Lignosulfates bonding agents can be used, as well polyurethane food grade adhesives such as urethane, melaminic and phenolic resins.

15 Claims, 8 Drawing Sheets

MOLDED OR EXTRUDED CORK COMPOSITE AND METHOD OF MANUFACTURING COMPRESSED CORK PET PRODUCTS AND PET TOYS MADE FROM THE SAME

RELATED APPLICATIONS

The present invention claims benefit of U.S. Provisional Application No. 61/806,417, filed on Mar. 29, 2013 and incorporated by reference as if fully rewritten herein.

BACKGROUND OF THE INVENTION

1. Field of the Invention

The present invention relates generally to pet products formed of a cork composite material and a method for making the same and, more particularly, to such materials and methods that include the delivery of aromatic attractant for encouraging domestic pet interaction.

2. Description of the Related Art

There are many pet products available that attempt to provide decorative and/or functional covers or surfaces. One example includes a covered bowls such as pet food and water bowls as described in U.S. Pat. No. 8,286,589 B1, issued to the present inventor. While such products anticipate the use of non-skid surfaces for placement on metal pet feeders, such technology not only is not readily adaptable to other types of pet products, but also lacks aesthetic and design versatility that is desirable for various applications.

The parent application identified above, which is incorporated by reference as if fully rewritten herein, relates generally to pet products that include the delivery of catnip aromatic attractant for encouraging pet interaction and, more particularly, to such a pet toys formed of a catnip composite and a method for making the same. However, in addition it has been found that such a cork composite material can be very advantageous as a fascia, covering, insert or construction material for a number of different, non-toy pet related products. As such, the present invention can provide a versatile, durable, and decorative material for a number of applications in addition to toys, such as food bowl coverings, mats (for placement under litter boxes or feeders), furniture, scratchers, and other products with which domestic pet, and particularly felines, are intended to interact.

These, among other disclosed advantages and features, overcome many of the deficiencies outlined and inherent within the known prior art.

SUMMARY OF THE INVENTION

Therefore, it is an object of the present invention to provide a cork composite material incorporating a filler or extender that can include a catnip aroma and a method for making the same.

It is another object of the present invention to provide for such a cork-catnip composite that can be used to produce a variety of domestic pet related products.

It is yet another object of the present invention to provide a cork-catnip composite material capable of being molded, compressed, extruded or otherwise shaped into small or large sheets or bodies of structural, yet aromatic attractant material.

It is still another object of the present invention to provide a composite material that is naturally hydrophobic.

It is still yet another object of the present invention to provide for use of durable, warm, soft, skid resistant and resilient material for use in conjunction with domestic pet products that is formed substantially of natural ingredients.

It is yet still another object of the present invention to provide for the use of a catnip composite material that results in a soft, textured "feel" that can be grasped, clawed or chewed in a manner that is positively received by domestic pets.

Further, the present invention provides a hydrophobic, naturally mold resistant, nontoxic material that can be robustly incorporated into a variety of pet products and product surfaces Further still, the present invention provide a material that has a long lasting, positive aroma for domestic pets that can encourage use and interaction with those pet related products incorporating such material.

As described in one embodiment of the present invention, a cork-catnip composite material is provided that is capable of being molded, compressed, extruded or similarly processed into small or large bodies or sheets and allow for the economic manufacture of a variety of products for domestic pets, especially felines. Dried and granulated catnip (or similar olfactory attractant) is blended with a fill material such as powdered or granulated agglomerate cork material that is typically a waste product of cork stopper manufacturing. It is envisioned that similar materials can be alternately used, such as, for example, waste cedar wood shavings or sawdust or other types of lignocellulose material. The use of various types of low cost waste products or woody biomass materials have been found to effectively extend the economic viability of the compression molded catnip products available in the prior art. The blended chipped, granulated or powdered materials are then mixed with a bonding agent. An effective bonding agent has been found in the use of lignosufates. Lignosulfates can also be obtained as a recovered waste product from the wood or paper pulping industries, and further will make the completed product of an "all natural" construction. Other effective bonding agents are known and can be uses, such as, for example, polyurethane food grade adhesives including, but not limited to, urethane, melaminic and phenolic resins.

As described above, a low cost, all (or substantially) natural composite material can be formed economically into various shapes or structures. The blended, bonded material can be extruded, compressed or molded into shapes, sheets, or blocks that can be machined. Given the economy of using a composite material whose components have an overall lower blended cost that a material made substantially of 100% molded catnip, it is now possible to make much larger bodies, be it pet toys or larger structures, such as claw scratching posts, that provide the attractant benefit to the domestic feline of catnip.

The foregoing and other aspects will become apparent from the following detailed description of the invention when considered in conjunction with the accompanying drawing figures.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

It should be understood that the composite material of the present invention can be formed through a number of extrusion or compression methods to be adapted to various designs, including sheets, laminates, bulk shapes or net molded shapes, and that the present disclosure is intended to describe preferred embodiments of the present invention.

DESCRIPTION OF THE PREFERRED EMBODIMENTS

The best mode for carrying out the invention is presented in terms of its preferred embodiment, herein depicted within the Figures.

1. Detailed Description of the Figures

Before explaining the present invention in detail, it is important to understand that the invention is not limited in its application to the details of the construction illustrated and the formulations described herein. The invention is capable of other embodiments and of being practiced or carried out in a variety of ways. It is to be understood that the phraseology and terminology employed herein is for the purpose of description and not of limitation.

In the following detailed description of the preferred embodiment of the present invention, reference is made to the accompanying drawings which, in conjunction with this detailed description, illustrate and describe pet related products formed of an attractant-composite material accordance with the present invention. Referring now to the drawings, in which like referenced characters represent corresponding elements throughout the several views. Attention is first directed to FIG. 1 and FIG. 2, in which a composite material is shown being formed and compressed, respectively, of three main components: a solid attractant 10; a filler material 20; and a binding agent 30. In a preferred embodiment, the preferred solid attractant is a granulated catnip. Further, it is preferred that the solid attractant can be between about 10% to about 60% of the overall composition, by weight. Further, the preferred filler material is granulated or agglomerated cork, and it is preferred that the use of granulated or agglomerated cork is between about 80% to about 20% of overall composition, by weight. Alternate or additional filler materials are further anticipated, such as the inclusion of calcium carbonate, calcite or other organic or mineral based extenders or fillers. The inclusion of such materials can be selected to accommodate price, performance and design needs of any particular pet related item. Such criteria should be better apparent in conjunction with the additional description below.

Figure 1:
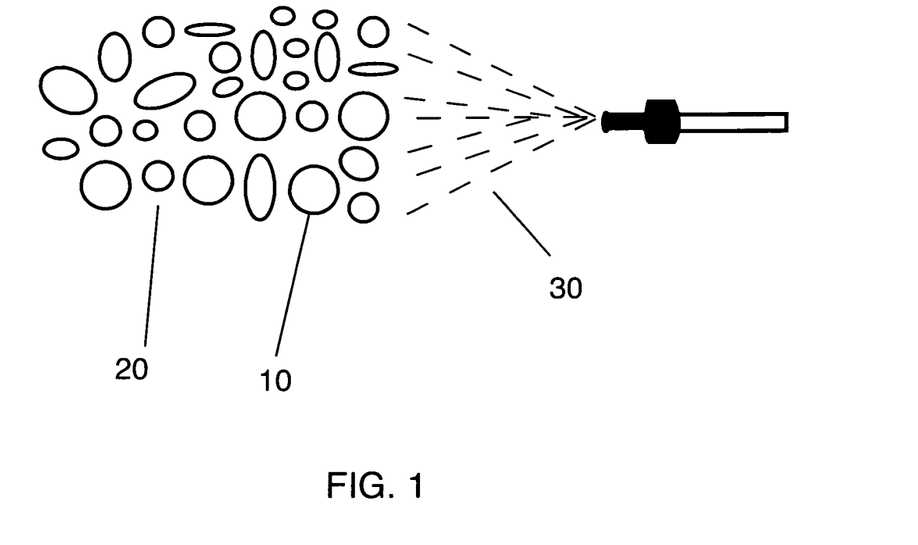
FIG. 1 is a schematic view of a cork-catnip composite material being formed according to an exemplary embodiment of the present invention.
Figure 2:
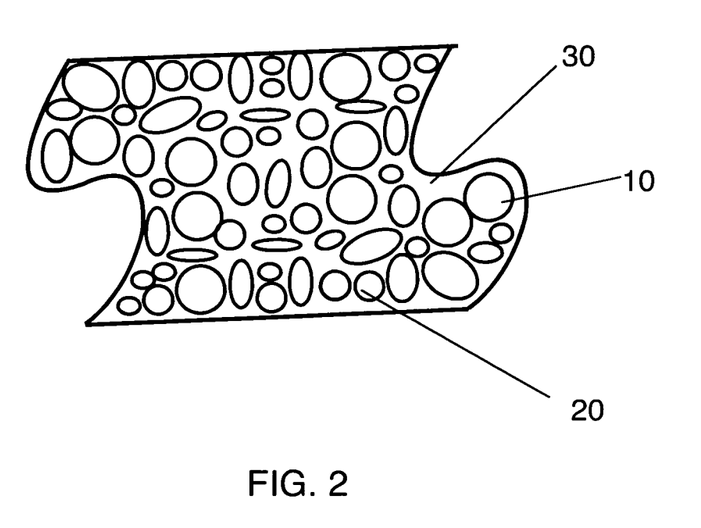
FIG. 2 is cross sectional view of the composite material made according to the exemplary method of FIG. 1.

Further still, the use of a binding agent is intended to be sufficient to maintain the composite material into the desired form and structure required for the particular design and intended use. It is further preferred that a binder be about 20% or less of the overall composition, by weight. A preferred binding is selected from those food grade polyurethanes, but other food grade adhesives including, but not limited to, dextrin, casein, gelatin, urea-formaldehyde, amine, and other urethane, melaminic and phenolic resins are know to also provide functional equivalency within the present teachings.

It is anticipated that other additives may be incorporated to accommodate particular uses or design choices, such as, for example, the incorporation of dyes in order to provide colors or otherwise alter the aesthetic of the final article. Other functional additives, such as odor absorbing materials, can further be incorporated into the agglomerated finished composite material. Such odor absorbing materials may include bentonite, zeolite, or other clays or odor absorbant materials. Again, the selection and function of such additional additives will be more apparent in conjunction with the additional description below.

A solid attractant 10 is preferably a dried and granulated catnip. It should be obvious to a person having ordinary skill in the relevant art, in light of the present teachings, that equivalent replacements for dried and granulated catnip can be utilized, including, but not limited to, any plant containing a terpenoid nepetalactone or similar chemical to the essential oil of *Nepeta cataria* and other species within the genus *Nepeta*, as well as other plants that are known to have effects on cats, including valerian (*Valeriana officinalis*) and plants that contain actinidine.

The filler material 20 is preferably granulated or agglomerated cork. Cork is commercially harvested from the bark tissue of the Cork Oak (i.e. *Quercus suber*). While a majority of the cork harvest is used each year in the manufacture of wine bottle stoppers and other closures, for the purpose of the present invention it is intended that less value added waste streams from such production be re-purposed. As such, it is intended that flaked, chipped, ground, agglomerate or manufacturing "dust" from other cork manufacturing processes are to be sourced and reused as the filler material 20 of the present invention. To date, such "powder" created from grinding or cutting in cork manufacturing has been burned in boilers for steam and energy production. Additional filler or extender materials, such as other lignocelluloses materials, are further anticipated. In addition to, or instead of granulated or agglomerated cork, the use of sawdust, wood chips, wood pellets, or wood shavings of cedar, pine or other lignocelluloses materials, as well as various woody biomass materials, may be utilized. The use of cedar or pine is preferred as an alternate material in that these all natural materials are already utilized in domestic pet products, such as for use in cat litter or small animal bedding, and their use is generally accepted by both pets and pet owners.

In the preferred embodiment, the binding agent 30 can be a lignosulfate binder, which has been found to be an effective bonding agent for both dried and ground catnip as well as for cork. Other effective bonding agents are known and can be uses, such as, for example, various thermoplastic resins and polyurethane food grade adhesives, dextrin, casein, gelatin, urea-formaldehyde, amine, and other urethane, melaminic and phenolic resins.

2. Operation of the Preferred Embodiment

As described in the present invention, a cork-catnip composite material is provided that is capable of being molded, compressed, extruded or similarly processed into small or large bodies or sheets and allow for the economic manufacture of toys and products for domestic pets, especially felines. As described above, a low cost, all (or substantially) natural composite material can be formed economically into various shapes. The blended, bonded material can be extruded, compressed or molded into shapes or sheets, and given the economy of using a composite material whose components have an overall lower blended cost that a material made substantially of 100% molded catnip. Further, the composite material can also be extended to have an overall lower blended cost that a material made substantially of 100% cork. It is now possible to make much larger bodies, be it pet toys or larger structures, such as claw scratching posts, that provide the attractant benefit to the domestic feline of catnip.

Figure 3:
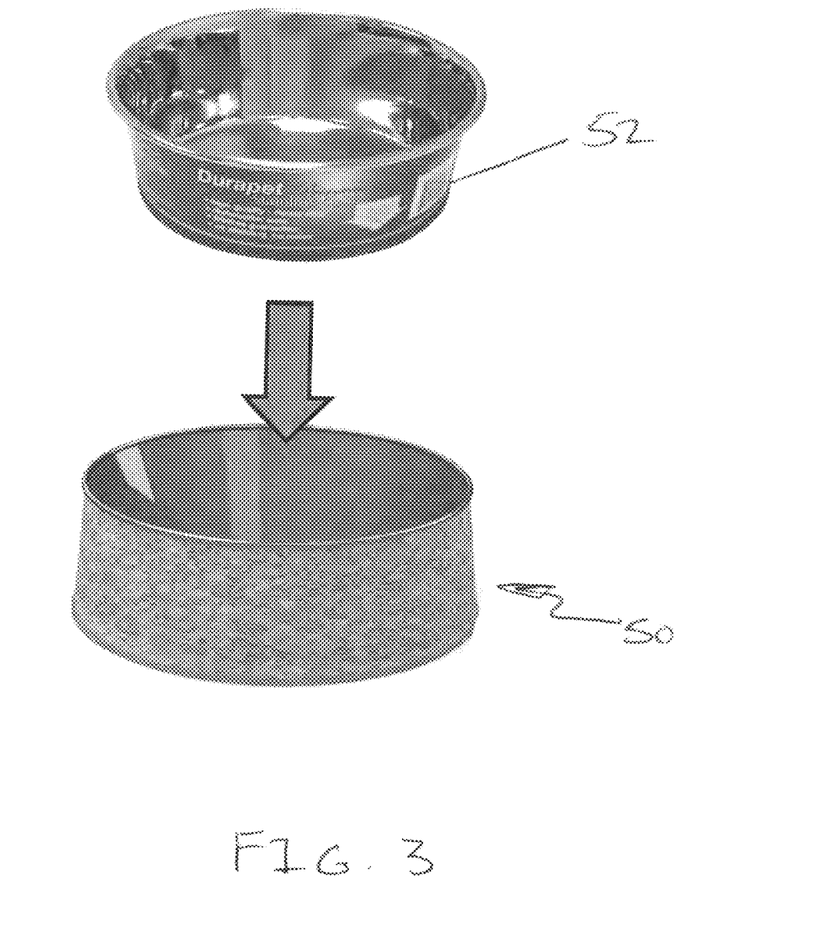
FIG. 3 is an exploded perspective views of a cover for use with a pet feeder or water bowl made according to the preferred embodiment of the present invention.
Figure 4:
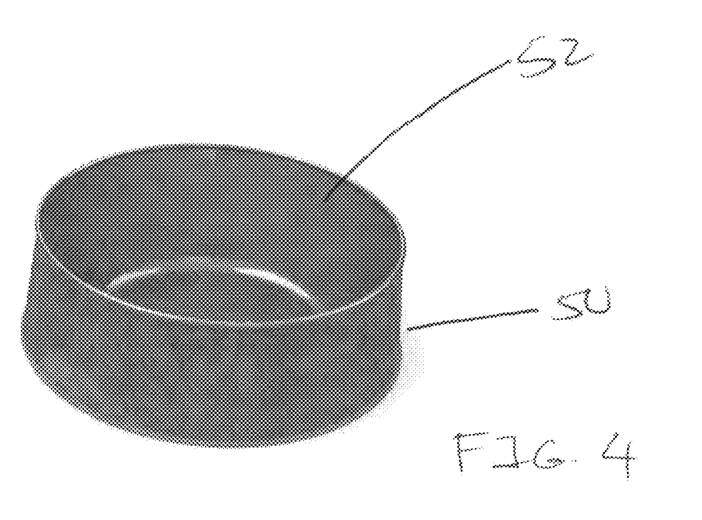
FIG. 4 is top perspective view thereof.
Figure 5:
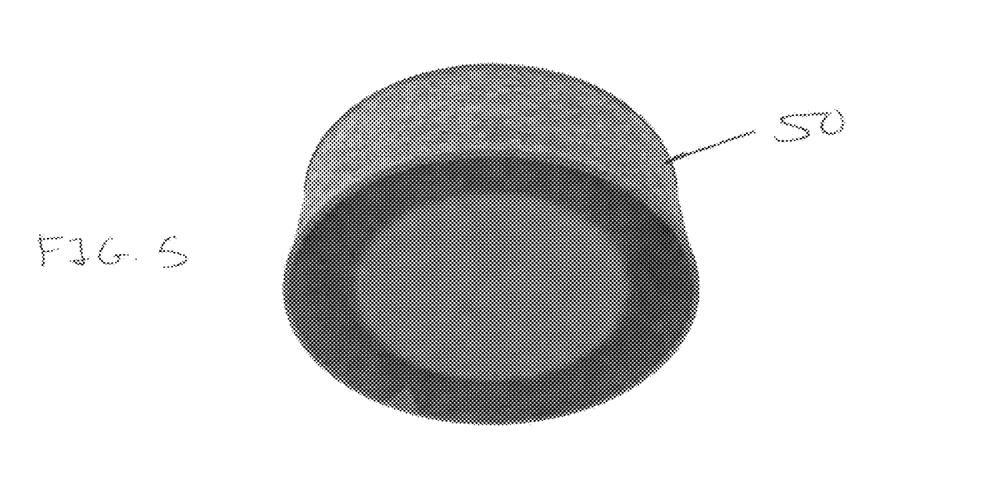
FIG. 5 is a bottom perspective view thereof.

Referring now to FIG. 3 through FIG. 5, an exemplary design for a cover 50 for use with a pet feeder or water bowl 52 is shown made according to the preferred embodiment of the present invention. In this exemplary design, a pet food and/or water bowl 52, such as a plastic or stainless steel pet feeder, is shown in conjunction with a cork composite material cover 50 that is preferably durable and lightweight, and provides an aesthetically pleasing appearance, protection to both the bowl and the surface on which the bowl may be set upon, and possibly some insulating properties to the contents placed therein. The use of a composite material incorporating a catnip or functional equivalent solid attractant may be agglomerated with a cork filler material and molded with a binding agent to provide a domestic pet feeder that is attractive to domestic pets, especially felines. Further, the consistency and texture of the cover 50 is quiet when contacted with hard surfaces, unlike a molded plastic body. Further, it is formed of a closed cellular structure that is hydrophobic and inhibits mold growth. The cover 50 may be placed about at least a portion of an exterior of the bowl, or completely encase the bowl sidewall. The cover 50 can remaining affixed to the bowl, or merely contact the bowl through an interference or friction contact fit. Further, an adhesive may be placed between the exterior of the bowl and the interior of the cover.

Figure 6:
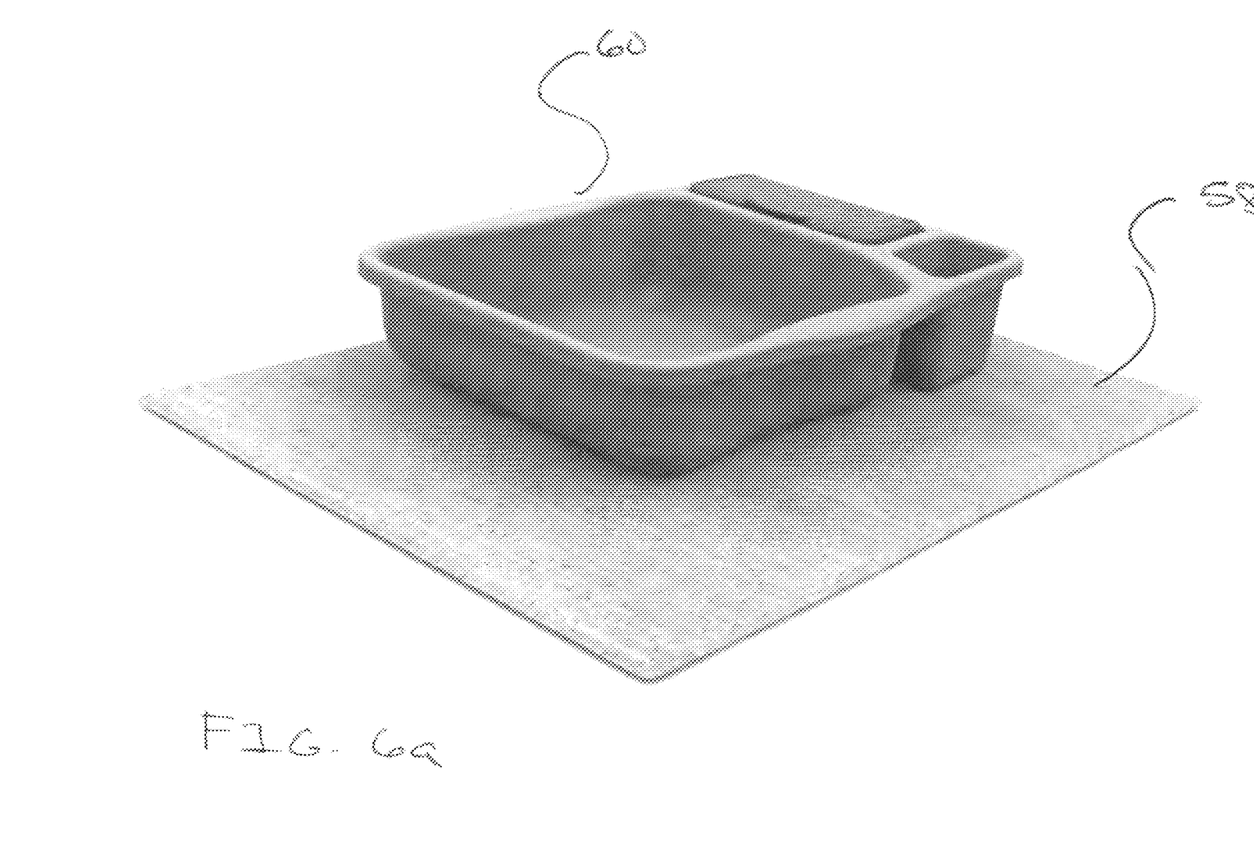
FIG. 6a is a perspective view of a underlayment mat made according to the preferred embodiment of the present invention for use in conjunction with a feline litter box.
FIG. 6b is a perspective view of a underlayment mat made according to the preferred embodiment of the present invention for use in conjunction with a pet feeder or water bowl.
Figure 6B:
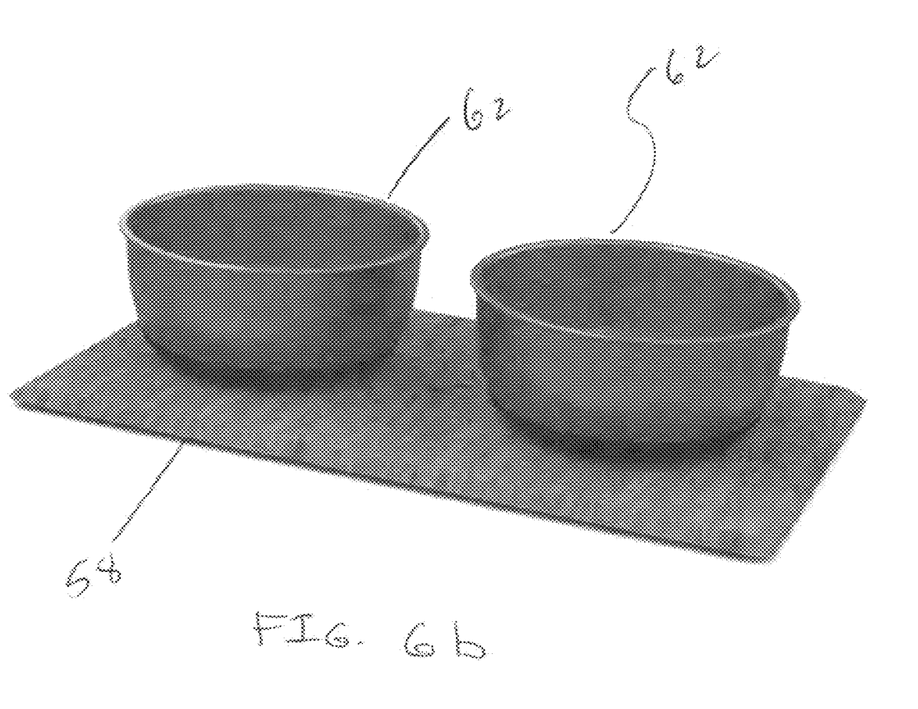

As shown in conjunction with FIG. 6a and FIG. 6b, exemplary designs for underlayment mats 58 are shown for use in conjunction with a small animal litter box 60 (FIG. 6a) or a pet feeder or water bowl (FIG. 6b), and incorporating the composite material according to the preferred embodiment of the present invention. The cork-catnip materials can further incorporate odor absorbing materials, as described above, to counteract the odors generated by use of a small animal litter box. Further still, the natural hydrophobicity of the cork materials will prevent water damage due to spills or overflow from the pet food and water bowls 62.

Figure 7A:
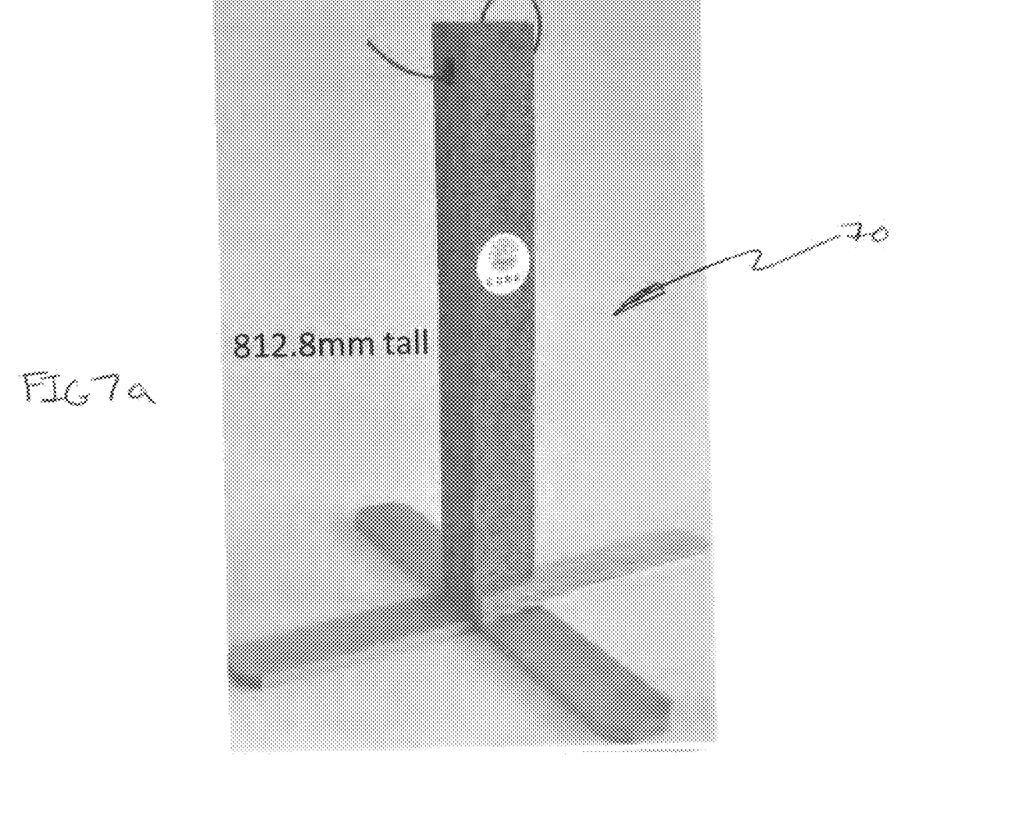
FIG. 7a through FIG. 7d are domestic cat scratchers incorporating the composite material according to the preferred embodiment of the present invention.
Figure 7B:
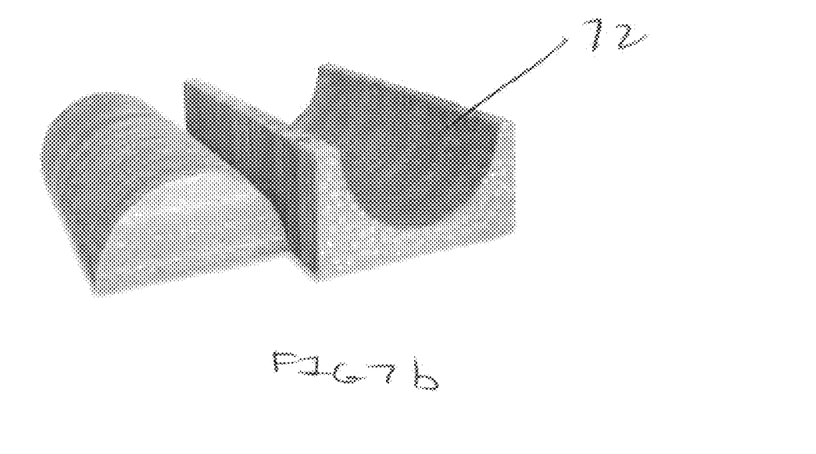
Figure 7C:
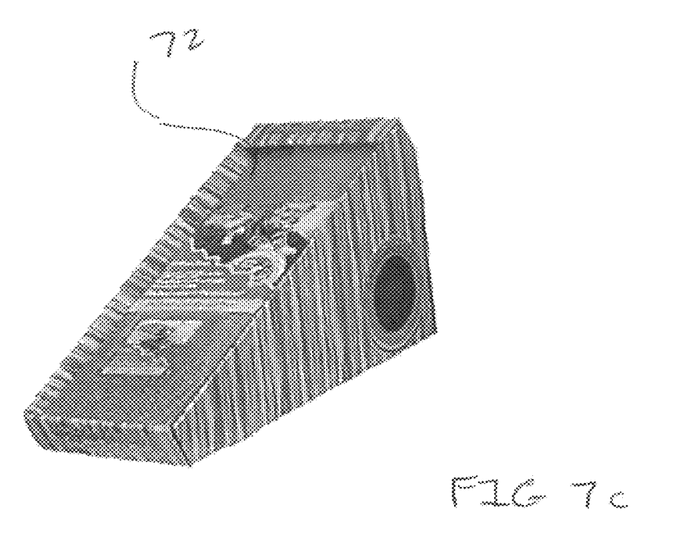
Figure 7D:
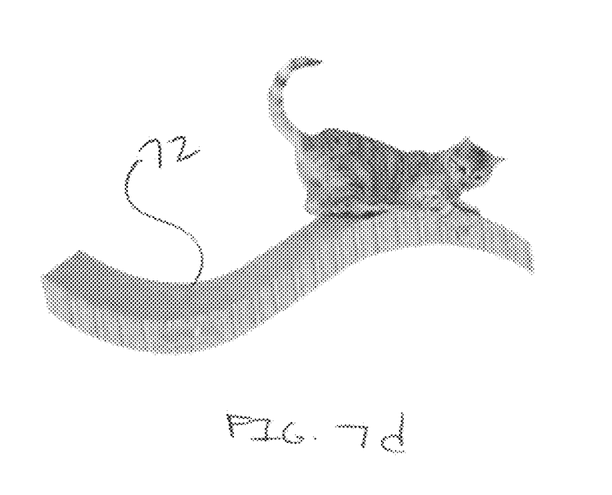
Figure 8A:
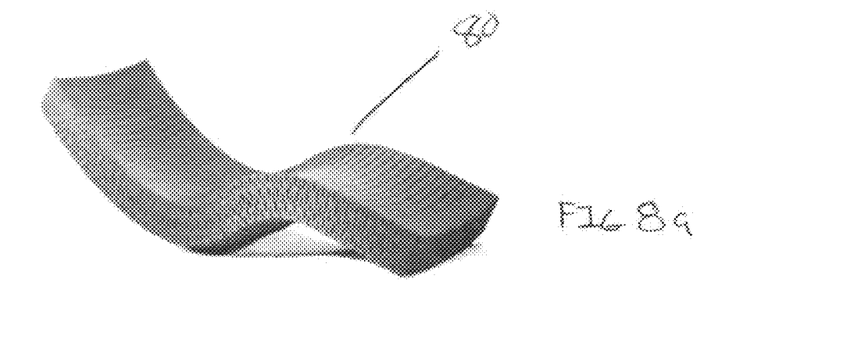
FIG. 8a through FIG. 8d are domestic pet furniture of alternate designs formed of the composite material according to the preferred embodiment of the present invention.
Figure 8B:
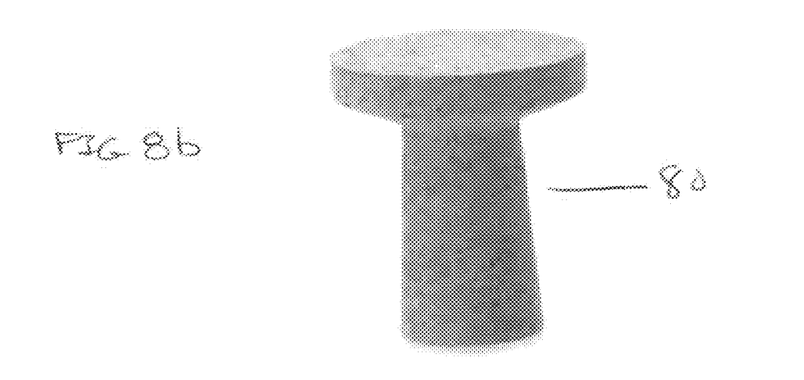
Figure 8C:
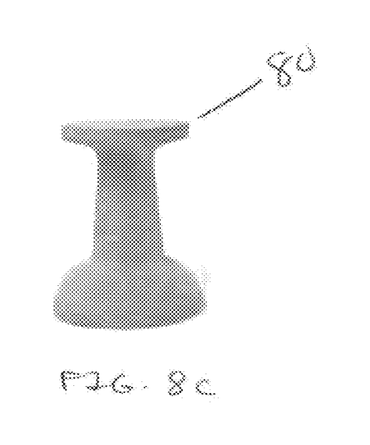
Figure 8D:
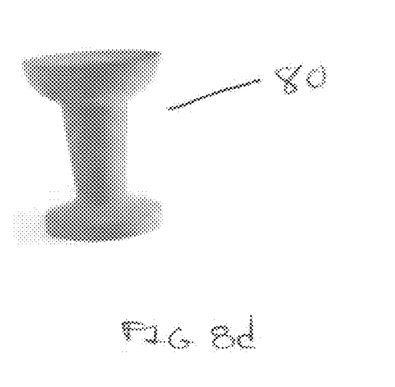

As shown in conjunction with FIG. 7a through FIG. 7d, exemplary designs for domestic cat scratchers are shown incorporating the composite material according to the preferred embodiment of the present invention. The cork-catnip composite material can be affixed as a functional surface element 72, as shown in FIG. 7b through FIG. 7d, or as assembled into a scratching post design 70, as shown in FIG. 7a.

As shown in FIG. 8a through FIG. 8d, domestic pet furniture 80 of alternate exemplary designs are shown further formed of the composite material according to the preferred embodiment of the present invention.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A moldable or extrudable cork composite material substantially comprising:
   a. a solid attractant, wherein said solid attractant is selected from the group consisting of: dried and granulated catnip; any plant containing a terpenoid nepetalactone; other species within the genus *Nepeta*; other plants that are known to have effects on cats; valerian (*Valeriana officinalis*); plants that contain actinidine; and, synthetic chemical derivatives similar to the essential oil of *Nepeta cataria*;
   b. granulated or agglomerated cork;
   c. a filler material, wherein said filler material is selected from the group consisting of: granulated cork; agglomerated cork; sawdust; wood chips; wood pellets; wood shavings of cedar; and, sawdust, wood chips, wood pellets, and wood shavings of pine; calcium carbonate; calcite; bentonite; zeolite; and other clays materials; and
   d. a binding agent;
wherein said composite material provides sufficient delivery aromatic olfactory attractant to be effective in having an interactive response with a domestic feline.

2. The composite material of claim 1, wherein said solid attractant comprises between about 10% to about 60% of the overall composition, by weight.

3. The composite material of claim 1, wherein said filler material comprises between about 80% to about 20% of overall composition, by weight.

4. The composite of claim 1, wherein said binding agent comprises about 20% or less of the overall composition, by weight.

5. The composite material of claim 1, wherein said binding agent is selected from the group consisting of: food grade polyurethanes; dextrin; casein; gelatin; urea-formaldehyde; amine; urethane resins; melaminic resins; phenolic resins; and lignosulfate binders.

6. The composite material of claim 3, wherein said solid attractant comprises between about 10% to about 60% of the overall composition, by weight.

7. The composite material of claim 6, wherein said filler material comprises between about 80% to about 20% of overall composition, by weight.

8. The composite of claim 7, wherein said binding agent comprises about 20% or less of the overall composition, by weight.

9. The composite material of claim 2, wherein said binding agent is selected from the group consisting of: food grade polyurethanes; dextrin; casein; gelatin; urea-formaldehyde; amine; urethane resins; melaminic resins; phenolic resins; and lignosulfate binders.

10. The composite material of claim 3, wherein said binding agent is selected from the group consisting of: food grade polyurethanes; dextrin; casein; gelatin; urea-formaldehyde; amine; urethane resins; melaminic resins; phenolic resins; and lignosulfate binders.

11. The composite material of claim 1, further comprising the incorporation of dyes in order to provide colors or otherwise alter the aesthetic of the final article.

12. An underlayment mat for placement under a pet food or water bowl formed substantially of a moldable or extrudable catnip composite material of claim 1.

13. The underlayment mat for placement under a small animal litter box substantially of a moldable or extrudable catnip composite material of claim 1.

14. A cat scratcher formed substantially of a moldable or extrudable catnip composite material of claim 1.

15. Pet furniture adapted for use with domestic pets formed substantially of a moldable or extrudable catnip composite material of claim 1.

* * * * *